United States Patent [19]
Diehl et al.

[11] 3,947,765
[45] Mar. 30, 1976

[54] AUTOMATED ELECTRICAL RESISTIVITY MEASURING APPARATUS FOR SEMICONDUCTOR CRYSTAL RODS

[75] Inventors: Joseph O. Diehl, Phoenix; Carl A. Germano, Scottsdale; Lawrence D. Mason, Phoenix; David R. Veres, Tempe, all of Ariz.

[73] Assignee: Motorola, Inc., Chicago, Ill.

[22] Filed: Jan. 30, 1975

[21] Appl. No.: 545,648

[52] U.S. Cl.............. 324/158 R; 324/62; 324/64; 324/158 F
[51] Int. Cl.² ............ G01R 27/02; G01R 27/08
[58] Field of Search.............. 324/158 R, 64, 51, 62, 324/13, 63, 158 F

[56] References Cited
UNITED STATES PATENTS

| | | |
|---|---|---|
| 2,586,125 | 2/1952 | Van Blarcom..................... 324/51 |
| 2,802,172 | 8/1957 | Mueller et al. ..................... 324/64 |
| 3,312,893 | 4/1967 | Currin et al. .......................... 324/64 |

*Primary Examiner*—R. V. Rolinec
*Assistant Examiner*—Ernest F. Karlsen
*Attorney, Agent, or Firm*—Henry T. Olsen; Harry M. Weiss

[57] ABSTRACT

A semiconductor crystal resistivity measuring station comprised of an enclosed automatically operated probe apparatus electrically connected to a remotely controlled power supply and an electronic computer for automatically executing precise electrical resistivity measurements, in consecutive increments along a single crystal length.

6 Claims, 4 Drawing Figures

AUTOMATED ELECTRICAL RESISTIVITY MEASURING APPARATUS FOR SEMICONDUCTOR CRYSTAL RODS

BACKGROUND OF THE INVENTION

1. Field of Invention

This invention relates to apparatus for measuring the electrical characteristics of crystalline solids from which semiconductor wafers are fabricated for the transistor and integrated circuit industry, and more particularly to apparatus which measures the electrical resistivity in successive increments of as-produced semiconductor crystals.

2. Description of Prior Art

In the manfacture of semiconductor crystals from which semiconductor wafers are fabricated, there is a process termed crystal pulling which involves dipping a seed crystal into a semiconductor melt and then slowly withdrawing the seed crystal. The process of crystal pulling involves alloying extremely minute amounts of a selected impurity into a crystal to enable it to exhibit required conductivity or resistivity characteristics. An increase in impurity concentration decreases the electrical resistivity characteristic of the raw manufactured crystal. Apparatus utilized in manufacture of semiconductor crystals requires a very stable, both mechanically and thermally, apparatus having provisions for alloying impurities at a very constant rate.

Recent emphasis has been placed on the development of methods and apparatus for accurately and automatically measuring electrical resistivity characteristics of semiconductor crystals produced by the crystal pulling process so as to quality categorize the raw crystal material for subsequent manufacture of semiconductor devices.

Prior art apparatus utilized in measuring the electrical resistivity of as-produced semiconductor crystals, for the purpose of determining relative crystal purity, were completely manual in operation for fixturing the crystal specimen within the resistivity probe apparatus. Mechanical arrangement of the probe apparatus made it difficult to load and unload the crystal specimen for rapid electrical resistivity measurements. Non-precise resistivity measurements were caused by voltage sensing probes that could not conform to the outer surface of the as-produced crystal, when actuated perpendicular to the crystal longitudinal centerline. Nonuniform electric current fields were created in the vicinity of the electrical contactors, which interfaced with the crystal body, providing the electric current field necessary for the resistivity measurements. Error was introduced into resistivity measurements due to visible light induced effects and stray electrical RF signals. A limitation was also placed on the allowable geometrical size of the crystalline solid which could be accommodated with the resistivity probe apparatus.

Prior art apparatus proved to be undesirable from the standpoint of relative ease of loading the crystal specimen, electrical interface contactor design which did not provide a uniform electric field in the vicinity of these contactors and light and heat energy induced effects in the electrical resistivity measurements derived from the environment of the resistivity test apparatus.

SUMMARY OF THE INVENTION

The foregoing and other shortcomings and problems of the prior art are overcome, in accordance with the present invention, by an automatically operated electrical resistivity measuring apparatus utilized for executing precise electrical resistivity measurements along a single as-produced crystal specimen.

According to an aspect of the present invention, fixturing apparatus is provided with the resistivity probe housing whereby a single crystal specimen is easily loaded into position and self aligned with respect to resistivity probe apparatus. A light cover and shield for attenuating stray energy is closed with respect to the probe housing, and all subsequent resistivity measuring operations are performed without manual intervention.

According to another aspect of the present invention, electrical contacts provide uniform contact to the full area of the crystal end surfaces thus providing the crystal rod with a uniform electric current throughout.

According to still another aspect of the present invention, an electrical probe having two electrodes each spaced apart at some preset distance measure the electrical voltage drop therebetween at successive increments along the entire length of the crystal specimen and thus accommodate for manufacturing irregularities along the length of the crystal.

In summary, the instant invention includes apparatus for rapidly loading a crystal specimen and then automatically measuring electrical resistivity at predetermined increments consecutively along a specified length of the raw crystal specimen.

The foregoing and other aspects of the present invention will be understood more fully from the following detailed description of an illustrative embodiment of the present invention in conjunction with the accompanying drawings, in which:

DESCRIPTION OF THE PREFERRED EMBODIMENTS

This system is a computer controlled, two point resistivity crystal measuring station designed to measure and record the electrical resistivity of a single crystal specimen without operator intervention. The crystal resistivity measuring station comprises two main pieces of apparatus electrically interconnected so as to provide computer control logic and remote controlled crystal current required to measure electrical resistivity in successive increments along a length of a raw crystal specimen. The resistivity crystal measuring station computer provides hardware control, status checking, in-process diagnostics, alarm routines, data acquisition, data manipulation and documentation.

Figure 1:
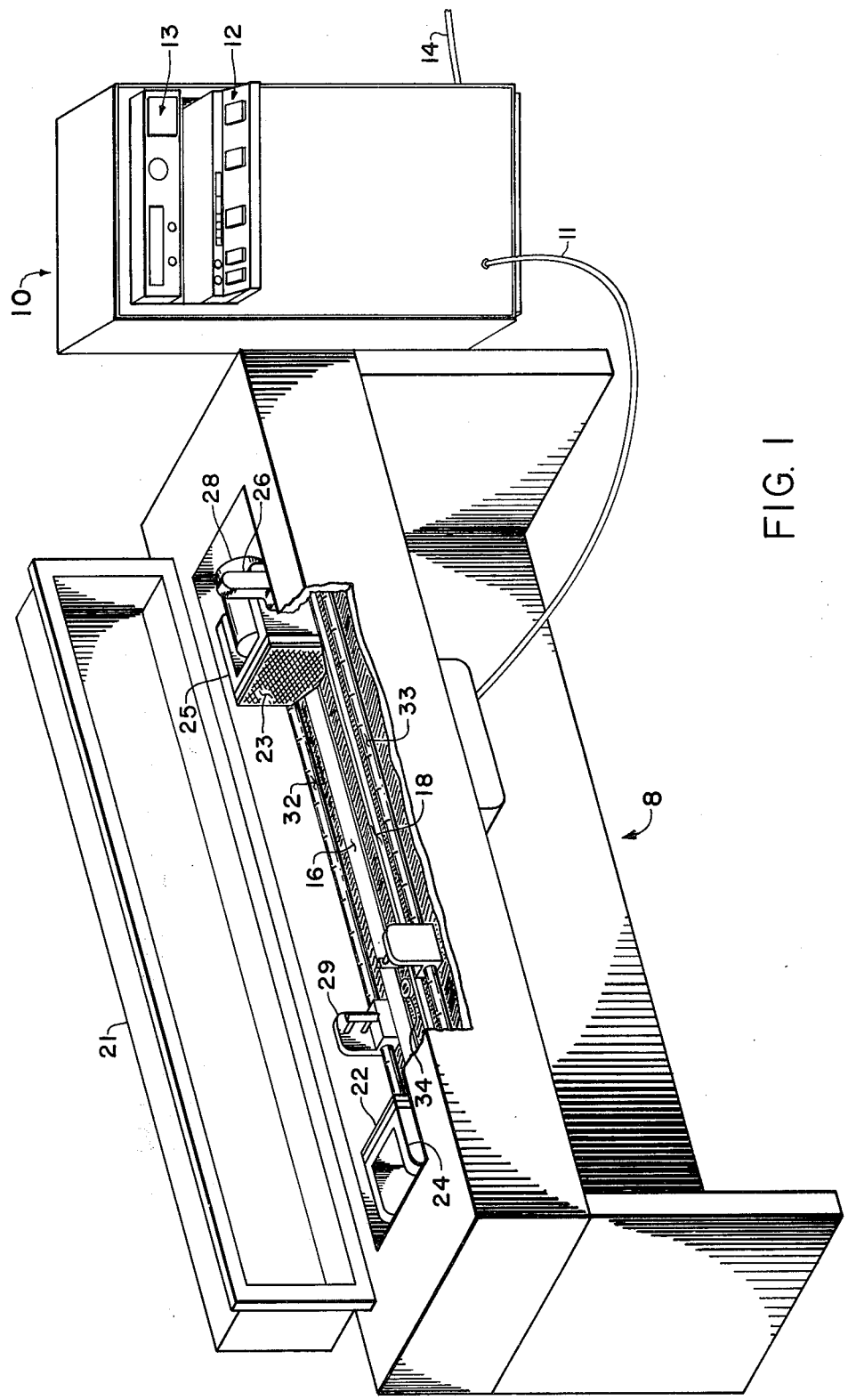
FIG. 1 shows an automatic resistivity probe sensing apparatus interconnected an electronics cabinet housing computer control unit.

Now referring to FIG. 1, a crystal resistivity measuring station comprised of a resistivity probe housing 8 and a computer control cabinet 10 interconnected via a common external bus 11. The computer control cabinet 10 contains a programmable desk top calculator 12, a crystal specimen interface control console 13, and is supplied with remote controlled power source through electrical cable 14.

In the preferred embodiment calculator 12 comprises a Hewlett-Packard Model 9820A with a 429 register memory option, magnetic card input, and ASCII interface card, all of which are not shown and located within electronics control cabinet 10. Calculator 12 drives external peripherals through common external bus 11 using ASCII coded format. The ASCII interface controller, located within control cabinet 10, selects the calculator ASCII bus, not shown, and delivers machine controlled commands for the appropriate peripheral hardware operations within resistivity probe housing 8.

More specifically, the resistivity probe housing 8 is provided with a permanently attached base structure upon which a pair of electrically insulated crystal support rails 16 and 18 are attached thereto in order to facilitate top loading of the crystal specimen with cover 21 in an open position. Resistivity probe housing 8 will mechanically accept a crystal specimen of cylindrical shape having a diameter up to 4 inches and a length from 6 to 30 inches. Electrical current is supplied to a crystal body through stationary electrical contact 22 and movable electrical contact 23. Contacts 22 and 23 are comprised of a metal screen mesh mounted on stationary and movable electrically insulated crystal contact supports 24 and 25, respectively. After the crystal is in proper placement in the resistivity probe housing 8, movable contact support 25 is coarsely adjusted to the crystal specimen length by manually adjusting carriage body 25 with carriage base handle 26. Ratchet and pawl mechanism, shown in FIG. 2, restrains carriage body 25 in close proximity to the crystal specimen. When the resistivity probe housing cover 21 is closed the crystal specimen is isolated from all visible light and stray electrical RF or electromagnetic signals. All subsequent operations for measuring the electrical resistivity of a crystal specimen are performed without manual intervention. Final or precision contact adjustment between a crystal rod and movable contact 25 is supplied by an air cylinder 28.

A probe carriage 29 moves relative to a pair of circular guide rods 32 and 33. Thus both resistivity probe carriage 29 and movable crystal contact support 25 can be appropriately positioned. Support rails 16 and 18 are tapered along a common edge and thereby utilized to cause the cylindrically shaped crystal rod to self align itself upon loading with respect to electrical crystal contacts 22 and 23. Generally depicted at 34 is a voltage probe adapted to move between spaced rails 16 and 18.

Figure 2:
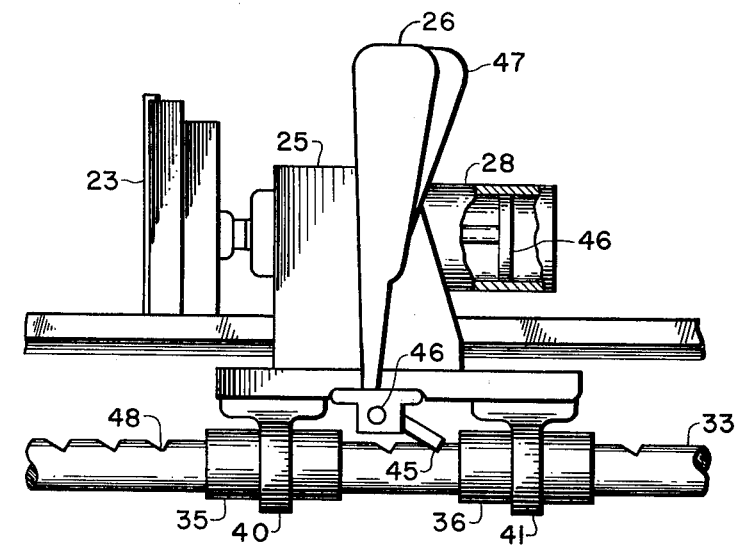
FIG. 2 shows a movable crystal specimen end support.

FIG. 2 shows in greater detail the movable crystal contact support 25 on the pair of circular guide rods, 32 and 33. A pair of linear ball bearings 35 and 36 are permanently fixed to crystal contact support 25 through mounting brackets 40 and 41, respectively. Coarse manual positioning of crystal contact support 25 is achieved by utilizing ratchet pawl 45 which is mechanically keyed to ratchet release mechanism 47 through a common shaft 46. A plurality of circular guide rod notches 48 are cut into circular guide rod 33 in incremental steps in order to receive ratchet pawl 45 during coarse positioning of movable crystal contact support 25. During final positioning air cylinder 28 under computer control is utilized to move piston 46 to further urge electrical contact 23 against the end of a crystal specimen so as to lock the crystal specimen between contacts 22 and 23 in preparation of the actual resistivity measuring cycle.

Figure 3:
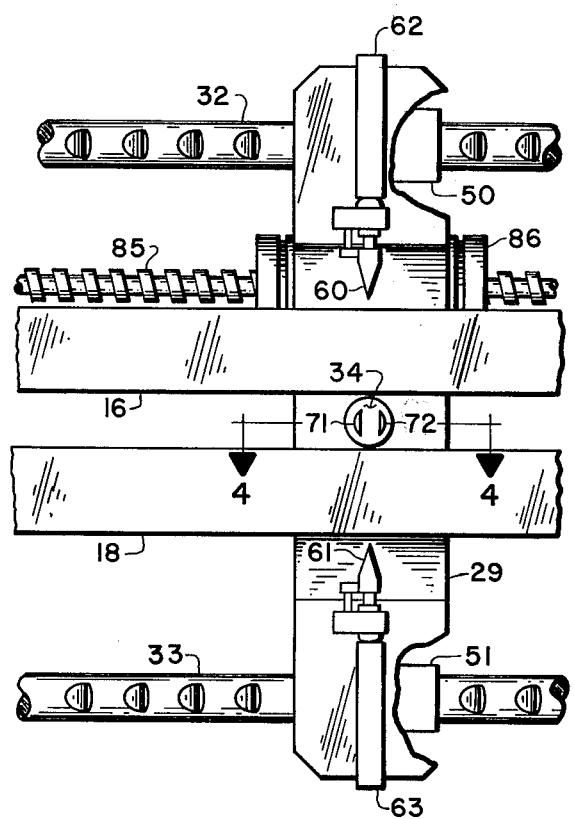
FIG. 3 shows a plan view of crystal specimen offset diameter sensors and voltage sensing probes.

FIG. 3 shows resistivity probe carriage 29 mounted on circular guide rods 32 and 33 through linear ball bearings 50 and 51, which are permanently fixed in resistivity probe carriage 29. Permanently mounted to the carriage base 29 are two air operated crystal diameter sensing wedges 60 and 61, which are directly coupled to electrical linear transducers 62 and 63. Also permanently mounted to the carriage base 29 are a pair of probe electrodes 71 and 72 through a common housing 80. Probe housing 80 is air operated to move between crystal rod support rails 16 and 18 for contacting the crystal specimen from below with probe electrodes 71 and 72.

A lead screw 85 is supported by ball bearings, not shown, mounted within resistivity probe housing 8 and directly driven by an electric motor, not shown. Probe carriage 29 actuation on linear ball bearings 50 and 51 is provided by a ball nut 86 which is permanently mounted to carriage base 29.

Figure 4:
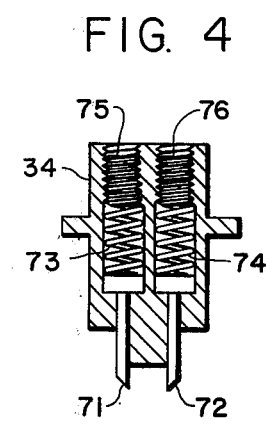
FIG. 4 shows a cross section of the voltage sensing probe shown generally on FIG. 3.

FIG. 4 shows in greater detail a cross section of probe housing 34 utilized for voltage measurements along the crystal rod. Electrodes 71 and 72 are individually spring loaded with springs 73 and 74, respectively. Electrodes 71 and 72 have an adjustable preloaded spring force through a set screw 75 and 76, respectively. Prior to loading a crystal specimen onto split tracks 16 and 18, the probe housing 34 resides in a lowered state. After loading suitable driving means, such as air cylinders, cam linkages, electric motors, etc., can be employed to raise the spring loaded probe electrodes into engagement with the crystal rod in anticipation of the actual electrical measuring cycle.

Various other modifications and changes may be made to the present invention from the principles of the invention described above without departing from the spirit and scope thereof, as encompassed in the accompanying claims.

What is claimed is:

1. A semiconductor crystal resistivity measuring station comprised of an enclosed probe apparatus electrically interconnected to a remotely controlled power supply and an electronic computer for automatically executing precise electrical resistivity measurements, in consecutive increments along a single crystal length, for similar crystal slices, said apparatus comprising:

a. at least two electrically insulated rails fixed with respect to said apparatus such that, upon loading a single crystal specimen for electrical resistivity measurements, the cylindrically shaped crystal is caused to be self aligned with respect to said apparatus;

b. at least two electrically insulated crystal specimen end supports, adjustable so as to accommodate crystal specimens of varying length, which provide a mounting base for electrical contacts of high density screen, or the like, continuously supported by flexible electrical insulating material and an electrical insulating pad; all mechanically fixed so as to interface prepared crystal specimen flats, normal to the crystal specimen longitudinal center line and on opposite ends, continuously;

c. and an encasement to isolate said apparatus from visible light, electrical RF signals, stray electromagnetic energy and heat transfer by convective air currents.

2. Apparatus providing the mechanical support and housing of a single as-produced semiconductor crystal as defined in claim 1 and further including two individually spring loaded electrode probes permanently captive within a common probe body which is actuated normal to the crystal specimen longitudinal center line making contact at two points along the crystal specimen surface for sensing an electrical voltage drop through successive incremental lengths of the crystal specimen.

3. Apparatus providing the mechanical support and housing of a single as-produced semiconductor crystal as defined in claim 1 and further including a means to determine the average geometrical cross-sectional area of the as-produced semiconductor crystal whose lengthwise incremental electrical resistivity is being measured.

4. Apparatus providing mechanical support and housing of a single as-produced semiconductor crystal as defined in claim 1 and further including a means for coarse adjustment, of at least one mechanical crystal end support comprising a ratchet release which is mechanically keyed to at least one mechanical ratchet pawl through a common shaft, a ratchet release guard mechanically mounted to said crystal end support base structure and a series of evenly spaced mechanical ratchet notches fixed parallel with crystal end support travel rod engaging said ratchet pawl keyed to said ratchet release; and at least one air cylinder whose piston is directly coupled to said crystal end support and when pressurized under program control is utilized to further urge electrical contacts against the end of the crystal specimen for final precise electrical contact positioning.

5. A semiconductor crystal resistivity measuring station comprising:
 a. a housing having a cover;
 b. a pair of electrically insulated rails forming a trough within said housing and beneath said cover whereby a cylindrically shaped crystal is caused to be centrally self aligned therein when placed on said rails;
 c. a pair of electrically insulated crystal specimen end supports, adjustable so as to accommodate crystal specimens of varying length, which provide a mounting base for electrical contacts of a high density screen for electrically and mechanically contacting the end surfaces of the cylindrical crystal; and
 d. means for applying electrical power to said screens whereby a uniform electric field is provided in said crystal.

6. A semiconductor crystal resistivity measuring station as recited in Claim 5 wherein one of said crystal end supports is manually adjustable by ratchet release means.

* * * * *